(12) United States Patent
Staib et al.

(10) Patent No.: US 8,131,474 B2
(45) Date of Patent: Mar. 6, 2012

(54) METHOD AND SYSTEM FOR INVESTIGATING GLUCOSE METABOLISM

(75) Inventors: Arnulf Staib, Heppenheim (DE); Johannes Pill, Leimen (DE); Reinhard Kotulla, Lambsheim (DE); Reiner Hegger, Bad Vilbel (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1228 days.

(21) Appl. No.: 11/276,816

(22) Filed: Mar. 15, 2006

(65) Prior Publication Data

US 2006/0253067 A1  Nov. 9, 2006

(30) Foreign Application Priority Data

Mar. 15, 2005  (DE) .......................... 10 2005 011 755
Jul. 16, 2005  (DE) .......................... 10 2005 033 358

(51) Int. Cl.
*G01N 33/48* (2006.01)
(52) U.S. Cl. ............ 702/19; 702/22; 702/179; 702/189; 703/2; 435/14; 436/14; 436/95; 708/442
(58) Field of Classification Search .................. None
See application file for complete search history.

(56) References Cited

U.S. PATENT DOCUMENTS

| | | | |
|---|---|---|---|
| 5,482,035 A | 1/1996 | Paloheimo | |
| 5,507,288 A | 4/1996 | Böcker et al. | |
| 5,712,801 A | 1/1998 | Turcott | |
| 5,846,189 A * | 12/1998 | Pincus .......................... | 600/301 |
| 6,272,480 B1 | 8/2001 | Tresp et al. | |
| 6,308,094 B1 | 10/2001 | Shusterman et al. | |
| 6,409,675 B1 | 6/2002 | Turcott | |
| 2002/0111754 A1 | 8/2002 | Lange et al. | |

FOREIGN PATENT DOCUMENTS

| EP | 1 102 194 A2 | 5/2001 |
|---|---|---|
| WO | WO 00/65366 | 11/2000 |
| WO | 2004/043230 A2 | 5/2004 |

OTHER PUBLICATIONS

Kroll, "Biological variation of glucose and insulin includes a deterministic chaotic component", 1999, BioSystems, vol. 50, pp. 189-201.*
Mehnert et al., "Diabtologie in Klinik und Praxis", 5th Ed, Thieme Verlag, Stuttgart, Germany, p. 71-72 (2003)—Partial translation of the book—p. 71, last paragraph of left column to p. 72, left column, first paragraph (relevant sections).
Aguirre, Luis Antonio, Barros, Vinicius C., and Souza, Alvaro V.P., "Nonlinear multivariable modeling and analysis of sleep apnea time series," Computers in Biology and Medicine, vol. 9, No. 3, May 1999 pp. 207-288.
Jaremko, Jacob et al. "Advances Toward the Implantable Artificial Pancreas for Treatment of Diabetes"; *Diabetes Care*, vol. 21, No. 3, p. 444-450 (Mar. 1998).
Smith, A.F.M. et al. "Monitoring Kidney Transplant Patients"; *Institute of Statisticians, Meeting on Practical Bayesian Statistics*, Cambridge, p. 21-24 (Jul. 1982).
Millsaps, Knox et al. "A Mathematical Model for Glucose-Insulin Interaction"; *Mathematical Biosciences*, vol. 23, p. 237-251 (1975).

* cited by examiner

*Primary Examiner* — Carolyn L. Smith
(74) *Attorney, Agent, or Firm* — Faegre Baker Daniels

(57) ABSTRACT

The invention relates to a method for investigating the glucose metabolism of a human being for disease-relevant and/or disease-related particularities. The glucose concentration g(t1) to g(tn) of a body fluid is measured at time points t1 to tn that are distributed over a period of at least six hours. The data points are then determined in phase space coordinates from the glucose concentration measuring values g(t1) to g(tn). The data points are then processed to highlight disease-relevant and/or disease-related particularities of the glucose metabolism of the investigated human being. The processing of the data points can be implemented by plotting them in a phase space representation or by determining from the data points a disturbance parameter that is correlated to the severity of a disturbance of glucose metabolism.

30 Claims, 10 Drawing Sheets

METHOD AND SYSTEM FOR INVESTIGATING GLUCOSE METABOLISM

REFERENCE TO RELATED APPLICATIONS

The present application is a based on and claims priority to German Patent Application No. DE 10 2005 011 755.4, filed Mar. 15, 2005 and German Patent Application No. DE 10 2005 033 358.3, filed Jul. 16, 2005, which are hereby incorporated by reference in their entirety.

TECHNICAL FIELD

The invention relates to a method for investigating the glucose metabolism of a human being for disease-relevant and/or disease-related particularities. The invention also relates to a system for investigating the glucose metabolism of a human being with a measuring unit for measuring the glucose concentration of a body fluid.

BACKGROUND AND SUMMARY

Continuous monitoring of the blood glucose concentration, in which measuring values are obtained every few minutes, for example, are known in the prior art under the term of "continuous monitoring". The prior art discloses delivering of the insulin administrations required for the treatment of diabetes at optimal time and at optimal dosages in order to keep the blood glucose levels within narrow limits at all times similar to the case of a healthy person.

The blood glucose concentration of a patient is of extreme significance in medicine. Studies have shown that extremely severe long-term aftereffects of diabetes mellitus (going blind due to retinopathy, for example) can be prevented by carefully monitoring the blood glucose level and keeping it within narrow limits.

Methods, in which blood glucose concentration measuring values are obtained by continuous monitoring, are advantageous in this context in that an increase in the blood glucose concentration beyond a critical value can be counteracted in a timely fashion by the administration of insulin. In particular, the measuring values can be used as the basis for predictions of a future blood glucose concentration for a period of up to half an hour such that an increase in the blood glucose concentration can be prevented by timely administration of insulin.

Although diabetic diseases are widespread and cause serious damage, early and reliable diagnosis continues to be associated with considerable difficulties. Though overweight is known to be a risk factor for a diabetic disease, a reliable identification of pre-type 2 diabetics is not feasible as a rule.

The testing of persons suspected of bearing an increased risk of a type 2 diabetes disease through the so-called glucose clamp technique is a resource-consuming method for determining insulin resistance and therefore is done in specialized facilities only. A glucose clamp involves that the blood glucose concentration of a patient is set to an elevated value by means of a glucose infusion (e.g. to 125 mg/dl) and this value is kept as constant as possible by continuing the glucose infusions. The glucose infusion rate required to do so is a measure of how rapidly elevated blood glucose values can be lowered by increased insulin release by the body. If only a low glucose infusion rate is determined in a glucose clamp, it is taken as an indication of insulin resistance, e.g. the effect of insulin is clearly limited in extent. Insulin resistance often precedes the manifestation of type 2 diabetes by years. Recognized on time, insulin resistance can be managed by appropriate changes in the daily habits, such as e.g. quantity and composition of nutrition, and/or insulin sensitizers and the manifestation of diabetic disease can be prevented.

However, a serious disadvantage of a diagnosis based on a glucose clamp is related to the fact that adipose patients, for example, show increased insulin resistance, though this usually does not deteriorate any further, i.e. no pre-type 2 diabetes-status is manifest. In the latter case, there would be no indication for preventative treatment of type 2 diabetes both in terms of pharmacoeconomics and the inherent risks of any pharmacotherapy.

Reliable selection of the patients with a high risk of diabetes is not feasible by means of a glucose clamp. Though suitable therapies for the treatment of pre-type 2 diabetics would be available (insulin sensitizers with improvement of the lipid profile), there is a lack of suitable diagnostics in order to be able to use these treatment options timely and in a targeted fashion.

Prior art techniques have also included method based on drawing a single blood sample, followed by measuring the blood glucose content and an NMR spectrum for determining the lipid profile, and final classification of the risk of type 2 diabetes by combining the parameters thus measured. However, the lipid profile is determined by numerous transient factors and possible correlation between lipid profile and diabetes can be established in an evidence-based fashion at best, i.e. based on populations and is not necessarily applicable to an individual case. Consequently, this method also provides no early diagnosis of pre-type 2 diabetes at the desired reliability.

It is therefore one of the object of the invention to devise a way of early detection of disturbances of glucose metabolism.

The present invention includes the collection of a large number of blood glucose concentration measuring values that are relatively closely spaced in time. However, unlike the methods described above, the present invention is not concerned with predicting future blood glucose concentration values or optimally controlling insulin administrations, but rather with the diagnosis of disturbances, in particular disease-related disturbances, of glucose metabolism.

Yet another object of the invention is a method for investigating the glucose metabolism of a human being for disease-relevant and/or disease-related particularities.

Yet another object of the invention is a system for investigating the glucose metabolism of a human being for disease-related particularities comprising a measuring unit for measuring the glucose concentration and an analytical unit for determining from the glucose concentration measuring values.

In the following, reference shall be made to the blood glucose concentration without limiting the scope of the invention. Since the invention relates to the processing of data points rather than the actual measuring of a glucose concentration, the glucose concentration of any other body fluid, for example interstitial fluid or eye fluid, that can be measured by spectroscopic means can be used just as well.

As part of the invention, it was noted that early anomalies of glucose metabolism are characterized by increasing disturbance of the body's intrinsic mechanism for regulation of the blood glucose concentration. From this, the inventors concluded that the particularities of the regulatory mechanisms that are relevant for diagnosis cannot be investigated by a single measurement or a measurement over a short period of time of only a few minutes, since this provides only a snapshot of the complex dynamics.

The blood glucose concentration of a human being varies during the course of the day and is strongly dependent on the intake of food and on physical exercise. For this reason, a single blood glucose concentration measuring value is often not indicative of whether it was measured on an ill or a healthy human being. Only the dynamics of the regulatory system allow disease-related particularities to be recognized reliably.

According to the invention, the blood glucose concentration is measured for a period of at least four hours, preferably at least six hours, such that typical changes in the blood glucose concentration such as those that occur in the course of the day, for example after meals, and associated responses of the body's intrinsic regulatory mechanism can be detected.

A further insight of the inventors was that particularities of the body's intrinsic regulatory mechanism are difficult to recognize in a customary representation, in which the blood glucose concentration is plotted against time, but show up clearly in a phase space representation both for the human eye and for mathematical evaluation algorithms. The data points are determined in phase space coordinates from the blood glucose concentration measuring values $g(t1)$ to $g(tn)$.

In a phase space, in control engineering sometimes referred to as "state space", any possible state of a dynamic system can be represented by a point. For example, the phase space coordinates of a moving particle can comprises its location and momentum or its momentum and acceleration. It is an essential characteristic of a phase space that time is not a coordinate. The sequential states of the system over time form a line in phase space that is called trajectory and whose profile is characteristic of the dynamics of the system.

Obviously, a trajectory can be determined only by approximation in practical application, since the measuring values, on the one hand, are inevitably associated with measuring errors and, on the other hand, cannot be determined at infinite density. In the context of this application, trajectory shall be defined as a line in phase space that is determined from the data points and approximates the theoretical exact trajectory.

The so-called delay coordinates are another important example of phase space coordinates. In delay coordinates, the state of a dynamic system is characterized not by multiple state variables measured simultaneously (location and momentum of a particle, for example), but by multiple values of a single state variable measured at time points that differ from each other by a delay time $\tau$.

Suitable phase space coordinates for the present invention are, for example, the blood glucose concentration $g(t)$ and its rate of change $g'(t)$ or delay coordinates $g(t)$ and $g(t-\tau)$. If delay coordinates are to be used, it is best to select a delay time $\tau$ of between 10 minutes and 90 minutes, preferably between 15 minutes and 30 minutes.

Type 2 diabetes is a chronic metabolic disease that progresses through various stages. Each stage represents a certain pathological state of glucose metabolism and requires therapeutic measures that are specifically adapted to the manifest stage. A type 2 diabetes disease starts with disturbance of the body's intrinsic glucose level regulation mechanisms. This disturbance is manifested in the form of a slower counter-regulation upon food intake in combination with reduced initial insulin secretion by the pancreas. In the next stage, all endogenous insulin secretion upon food intake is reduced such that extensive hyperglycemias manifest. The endogenous insulin production is basically arrested in the subsequent stage such that the body's intrinsic regulation of the glucose level counteracts hypoglycemias only. In the final stage of the disease, even this endogenous regulatory mechanism is lost.

Various therapeutic measures are available for the treatment of these stages of type 2 diabetes, for example diet, oral medication to enhance the sensitivity to insulin, and insulin. The targeted use of these therapeutic measures requires so-called staging, i.e. a reliable diagnosis of the stage of disease that is manifest in the individual case. The present invention allows a reliable diagnosis to be made periodically such that individualized optimization of therapy in the context of staging is made possible.

Although existing diagnostic methods, such as measuring insulin secretion and insulin sensitivity, can be used for staging, the effort involved is prohibitive, not least because the individualized optimization of therapy implies the adaptation of the measures as often as possible.

The data points obtained upon application of the method according to the invention can be processed in a variety of ways in order to allow a physician to obtain a diagnosis more easily.

These and other features and advantages of the present invention will be more fully understood from the following detailed description of the invention taken together with the accompanying claims and drawings. It is noted that the scope of the claims is definitely by the recitations therein and not by the specific discussion of the features and advantages set forth in the present description.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment (s) of the present invention.

DETAILED DESCRIPTION

The following description of the preferred embodiment is merely exemplary in nature and is in no way intended to limit the invention or its application or uses.

Figure 1:
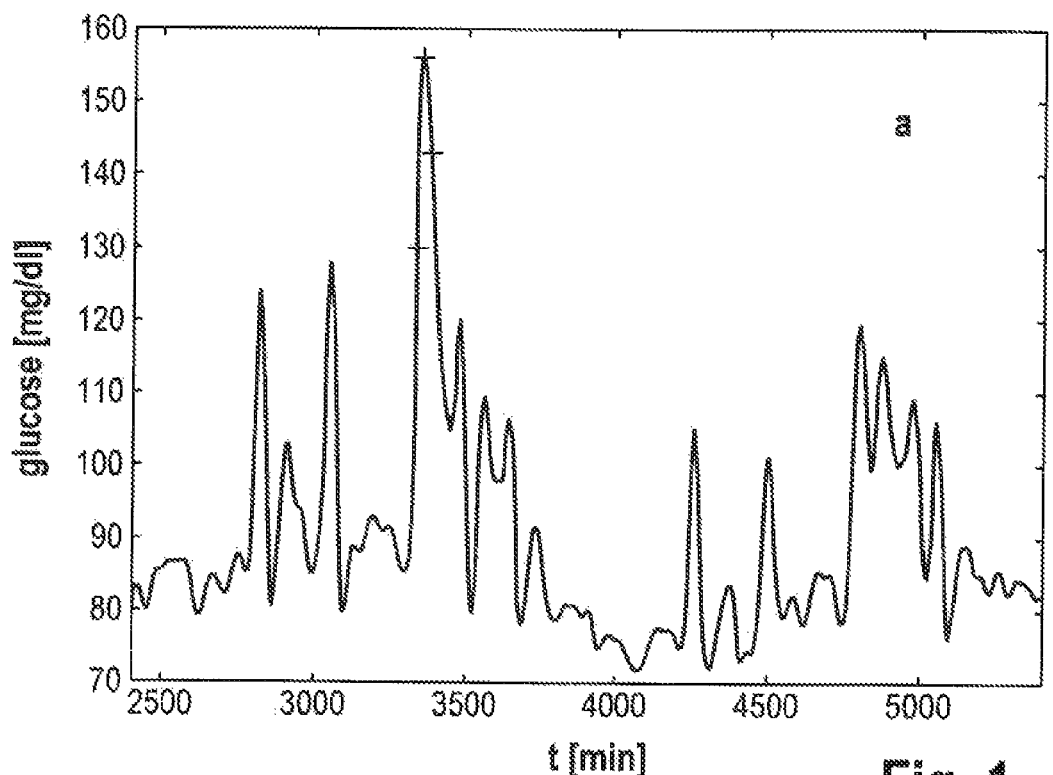
FIG. 1 shows a typical blood glucose concentration profile of a healthy subject.
Figure 2:
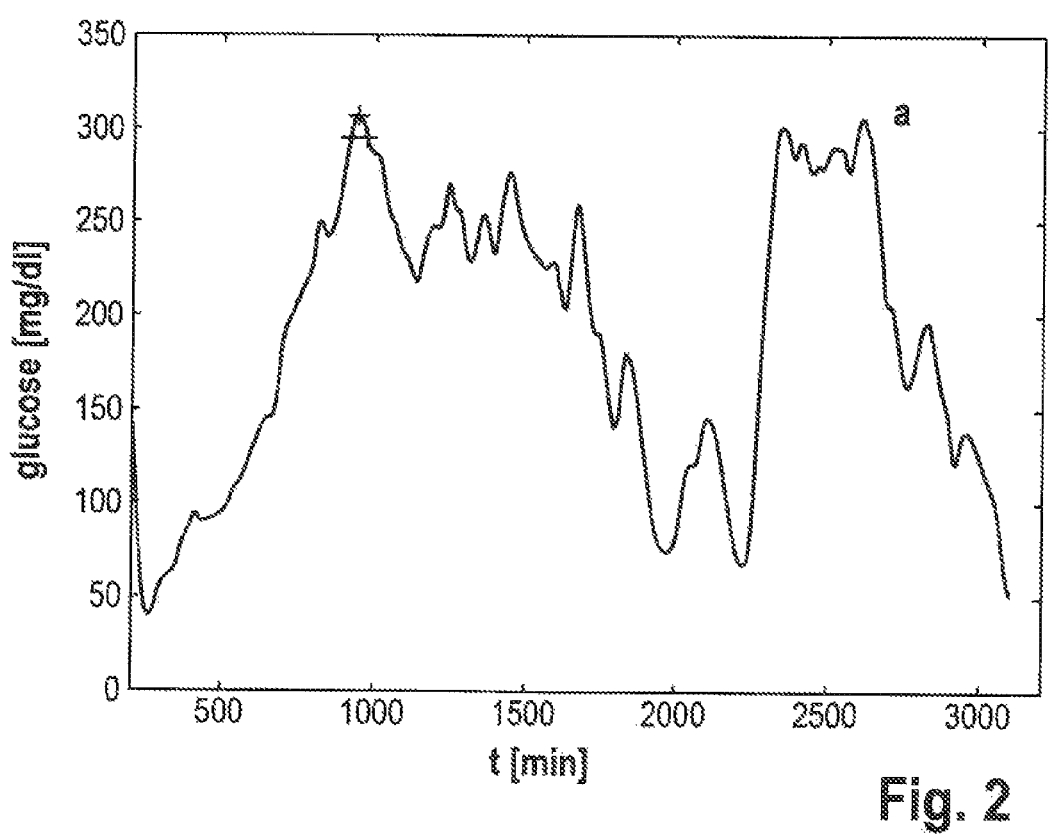
FIG. 2 shows a typical blood glucose concentration profile of a type 1 diabetic.
Figure 3:
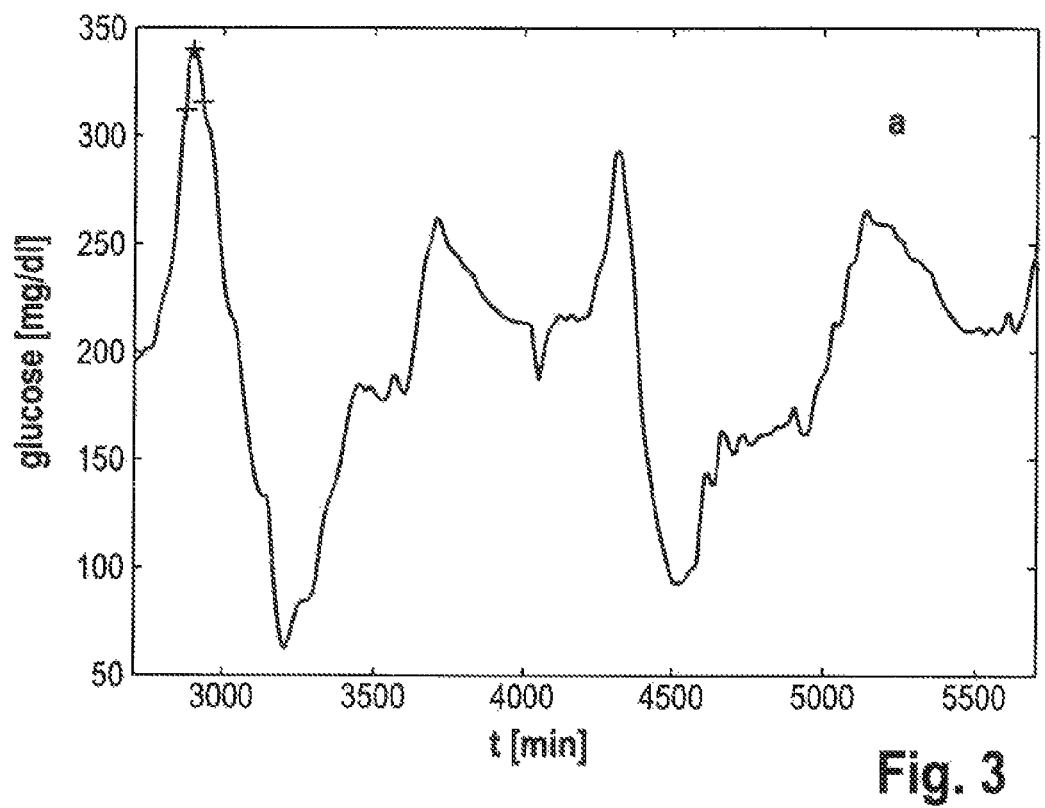
FIG. 3 shows a typical blood glucose concentration profile of a type 2 diabetic.

FIG. 1 shows a typical profile of the blood glucose concentration of a healthy subject over the course of approx. 50 hours. In the course of the day, the intake of meals and physical exercise cause significant variation in the blood glucose concentration g(t). It is evident that the blood glucose concentration is regulated to a target value of approx. 80 to 90 mg/dl glucose by the body's intrinsic regulatory system. For comparative purposes, FIG. 2 shows a typical profile of the blood glucose concentration of a type 1 diabetic over the course of 50 hours. Remarkable is the presence of concentration peaks in excess of 300 mg/dl glucose and the drop to values of less than 50 mg/dl. It can be concluded from these extremely large concentration variations that a disease-related disturbance of glucose metabolism is manifest. FIG. 3 shows a typical example of the blood glucose concentration profile of a type 2 diabetic in an advanced stage of the disease. Similar to the case of a type 1 diabetic, the presence of concentration peaks in excess of 300 mg/dl glucose permits to conclude directly that a disease-related disturbance of glucose metabolism is manifest.

Figure 4:
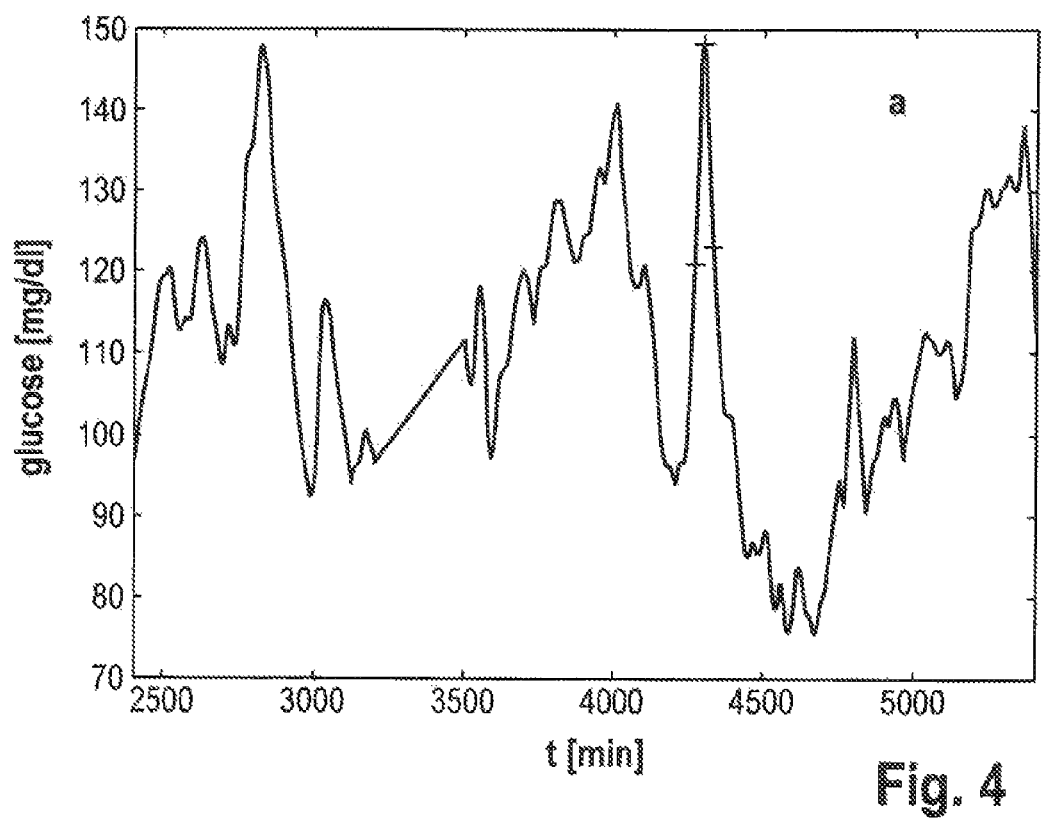
FIG. 4 shows a typical blood glucose concentration profile of a seemingly healthy pre-type 2 diabetic.

FIG. 4 shows the profile of the blood glucose concentration g(t) of a seemingly healthy subject, who in fact is a pre-type 2 diabetic in need of treatment. Like in a healthy subject (see FIG. 1), the blood glucose concentration is kept within a relatively narrow range of between approx. 80 mg/dl and 150 mg/dl by the body's intrinsic regulatory mechanism. Concentration peaks of 300 mg/dl blood glucose contents as are typical of diabetes and are present in FIGS. 2 and 3, for example, are not evident. For this reason, it is very difficult to diagnose the manifestation of pre-type 2 diabetes on the basis of the data shown.

Figure 5:
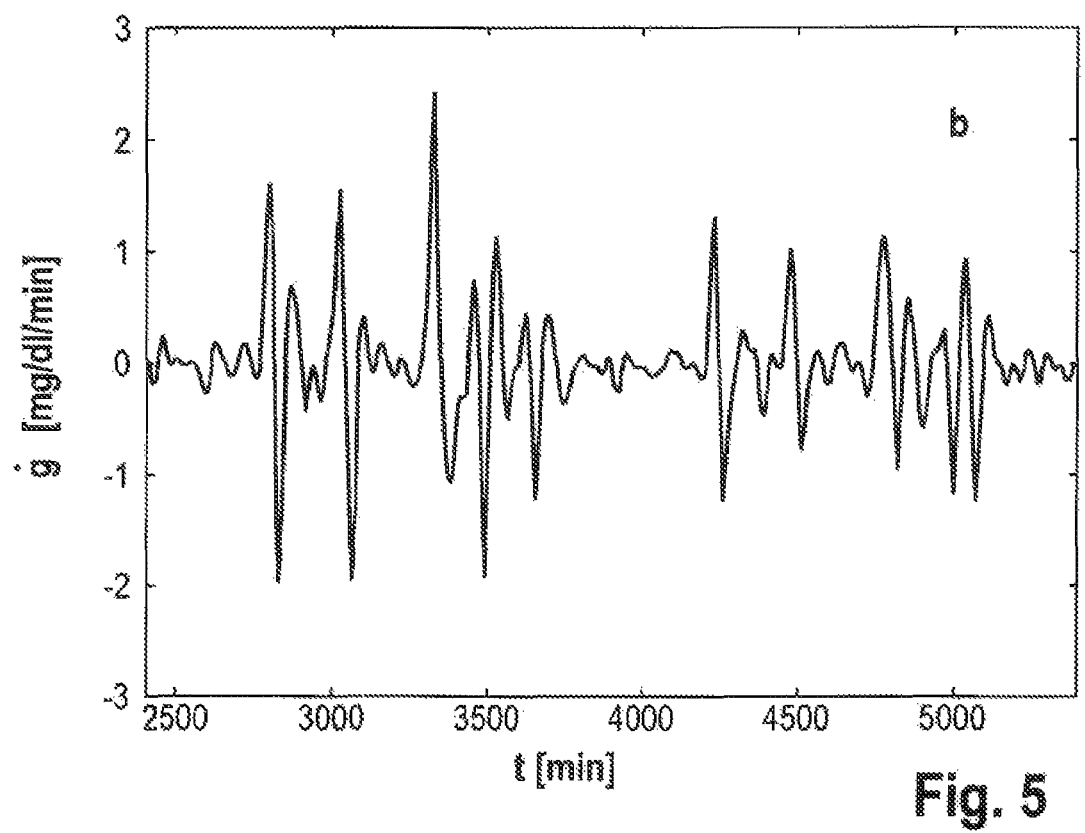
FIG. 5 shows the profile of the rate of change of the blood glucose concentration of the healthy subject shown in FIG. 1.

A widely accepted form of data processing consists of plotting not only the measuring parameter, i.e. the blood glucose in the present case, but also its derivative with respect to time. FIGS. 5, 6, 7, and 8 each show the rate of change of the blood glucose concentration in units of mg/dl/min for the blood glucose profiles shown in FIGS. 1 to 4. FIG. 5 is the plot of the derivative with respect to time of the blood glucose concentration of a healthy subject (as shown in FIG. 1), FIG. 6 of the type 1 diabetic, FIG. 7 of the type 2 diabetic and FIG. 8 of the pre-type 2 diabetic.

As is evident from these figures, the rate of change of the blood glucose concentration varies so much in the course of the day that its profile scarcely allows unambiguous information concerning the health status of a subject to be derived. In all figures shown, i.e. in healthy subject just as well as in diabetes patients, the rate of change of the blood glucose concentration varies between −2 and +2 mg/dl/min in the course of the day.

Data processing according to the invention allows the characteristic particularities of the data shown in the figures described above to be highlighted such that disease-related disturbances of glucose metabolism can be detected without difficulty. For this purpose, the measured blood glucose concentrations are used initially to determine data points in phase space coordinates.

Figure 9:
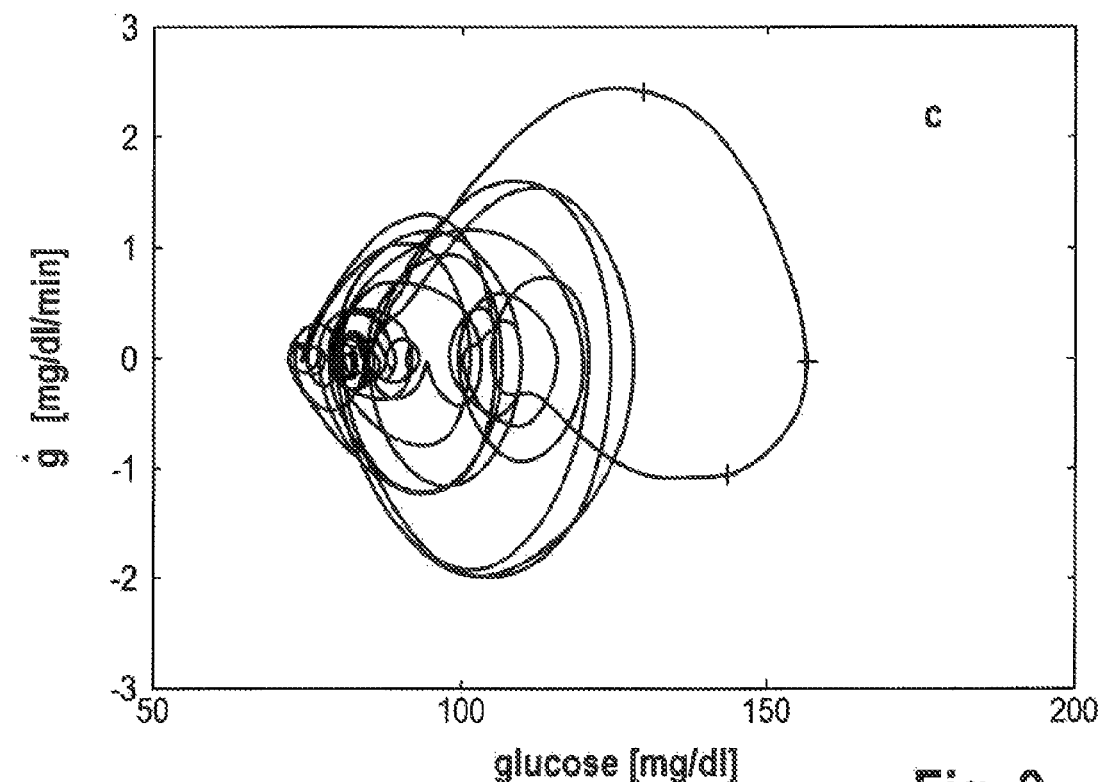
FIG. 9 shows a phase space representation of data points obtained from the blood glucose concentration values of the healthy subject shown in FIG. 1.
Figure 10:
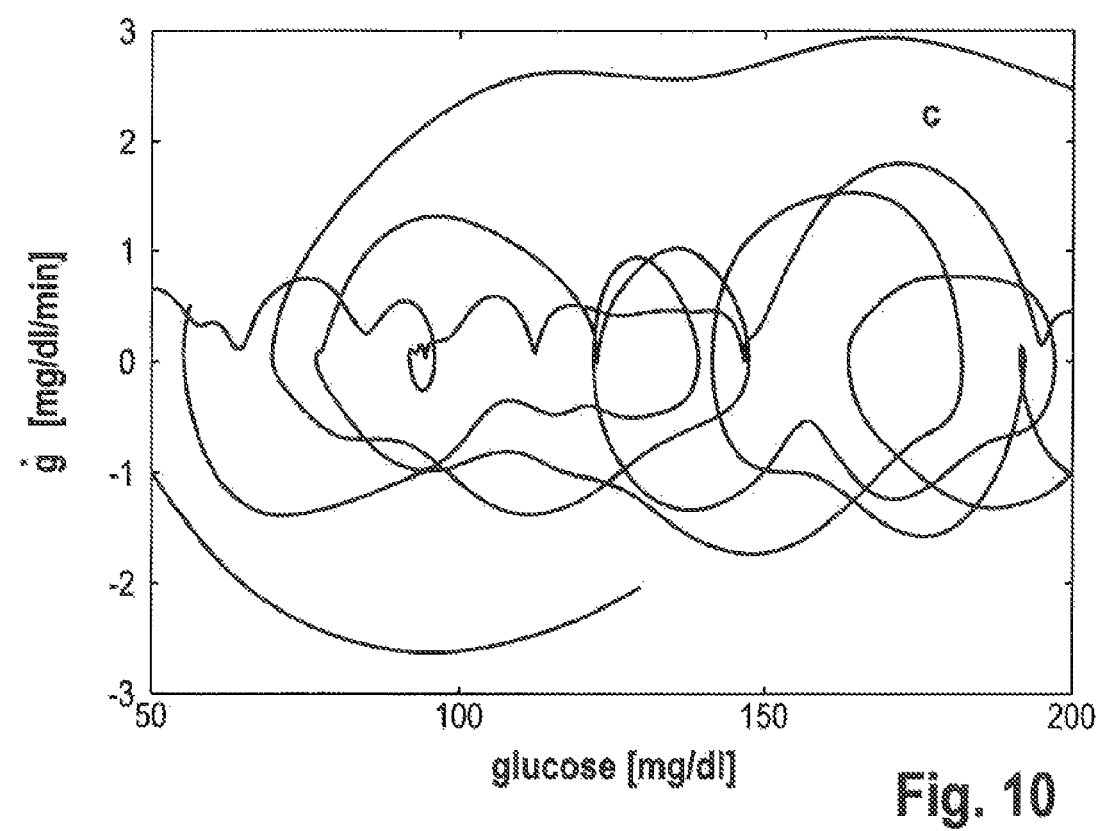
FIG. 10 shows a phase space representation of data points obtained from the blood glucose concentration values of the type 1 diabetic shown in FIG. 2.
Figure 11:
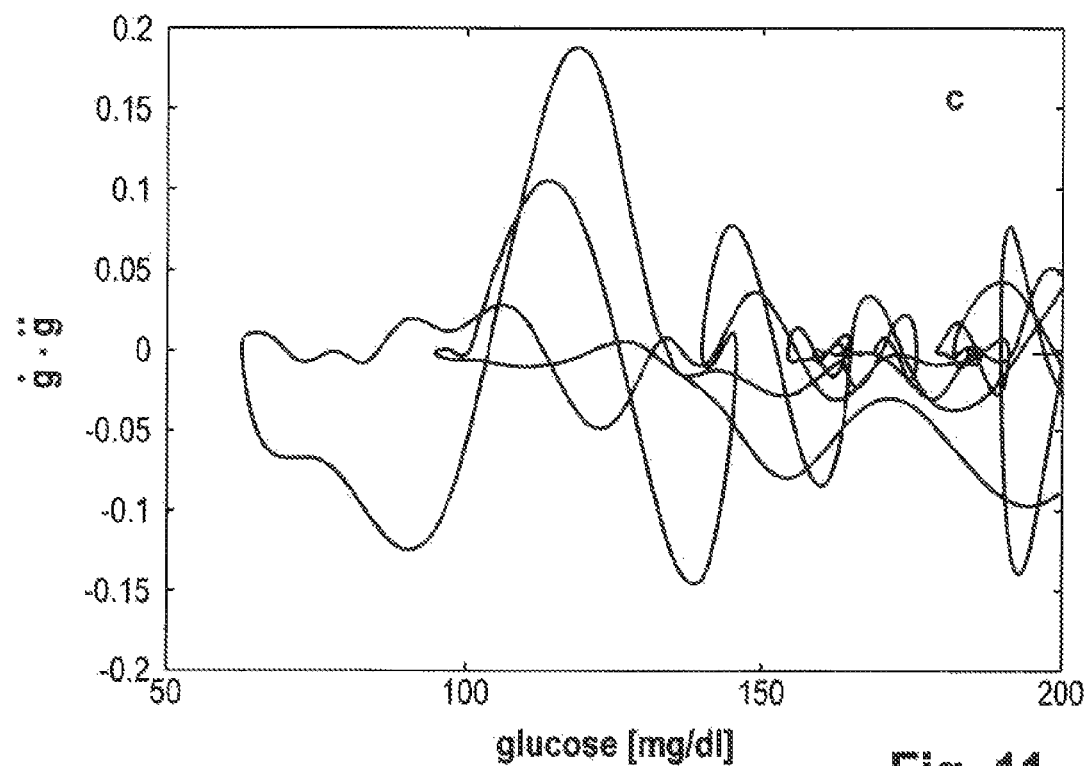
FIG. 11 shows a phase space representation of data points obtained from the blood glucose concentration values of the type 2 diabetic shown in FIG. 3.
Figure 12:
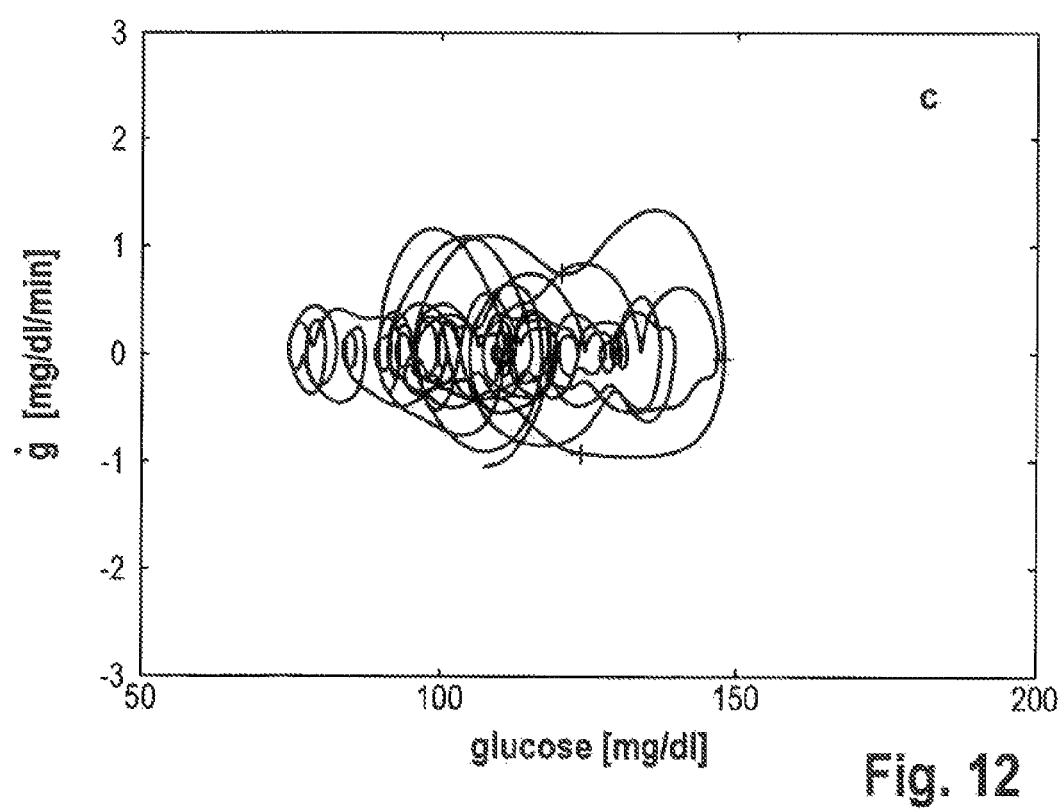
FIG. 12 shows a phase space representation of data points obtained from the blood glucose concentration values of the pre-type 2 diabetic shown in FIG. 4.

In FIGS. 9, 10, and 12, which shall be illustrated in more detail in the following, the blood glucose concentration and its rate of change at the corresponding time point are used as phase space coordinates. The blood glucose concentration g(t) and the product of its first and second derivative with respect to time were used as phase space coordinates in FIG. 11. The data points thus determined were plotted in a phase space representation for the series of measurements shown in FIGS. 1 to 4; in this phase space representation, the rate of change of the blood glucose concentration is plotted against the blood glucose concentration (FIGS. 9, 10, and 12) or the product of the rate of change and the second derivative with respect to time of the blood glucose concentration against the blood glucose concentration (FIG. 11).

The phase space representation of the data points of a healthy subject depicted in FIG. 9 shows a trajectory with a major number of loops that pass through a regulation point at approx. (90 mg/dl; 0 mg/dl/min). The various loops of the trajectory intersect in a very small volume element around this point at approx. 90 mg/dl±3 mg/dl such that the density of data points is increased in this place.

Figure 6:
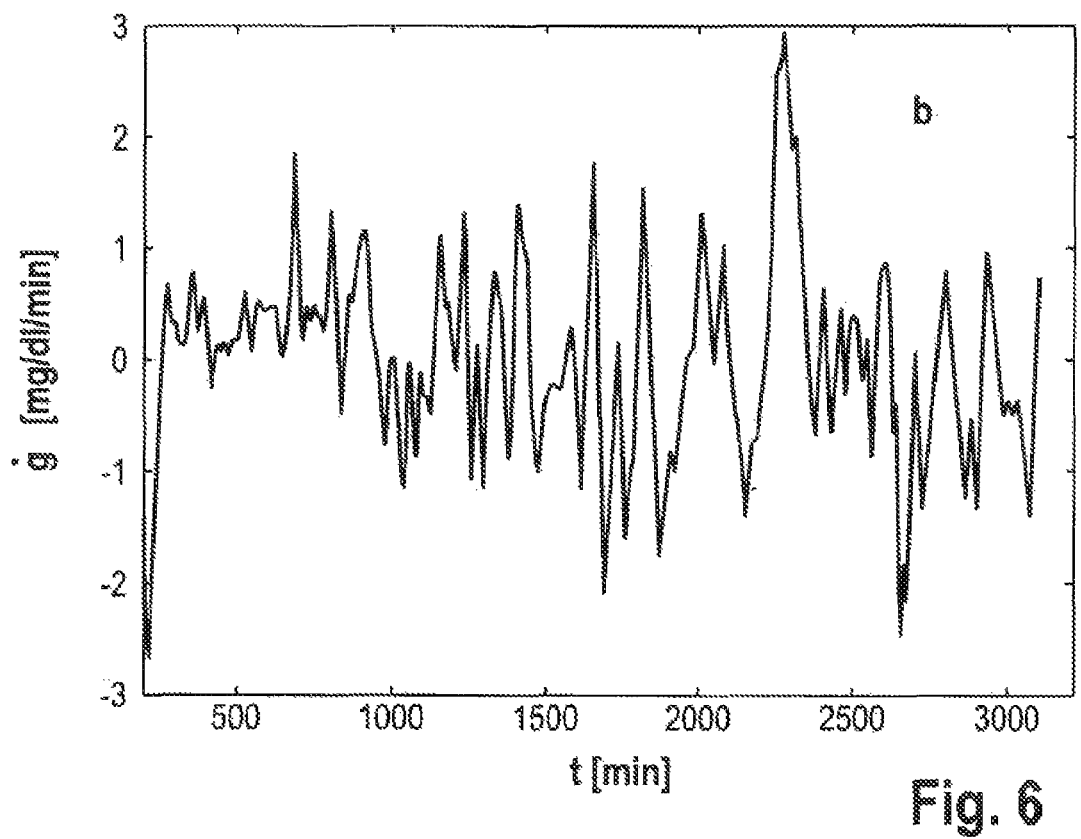
FIG. 6 shows the profile of the rate of change of the blood glucose concentration of the type 1 diabetic shown in FIG. 2.
Figure 7:
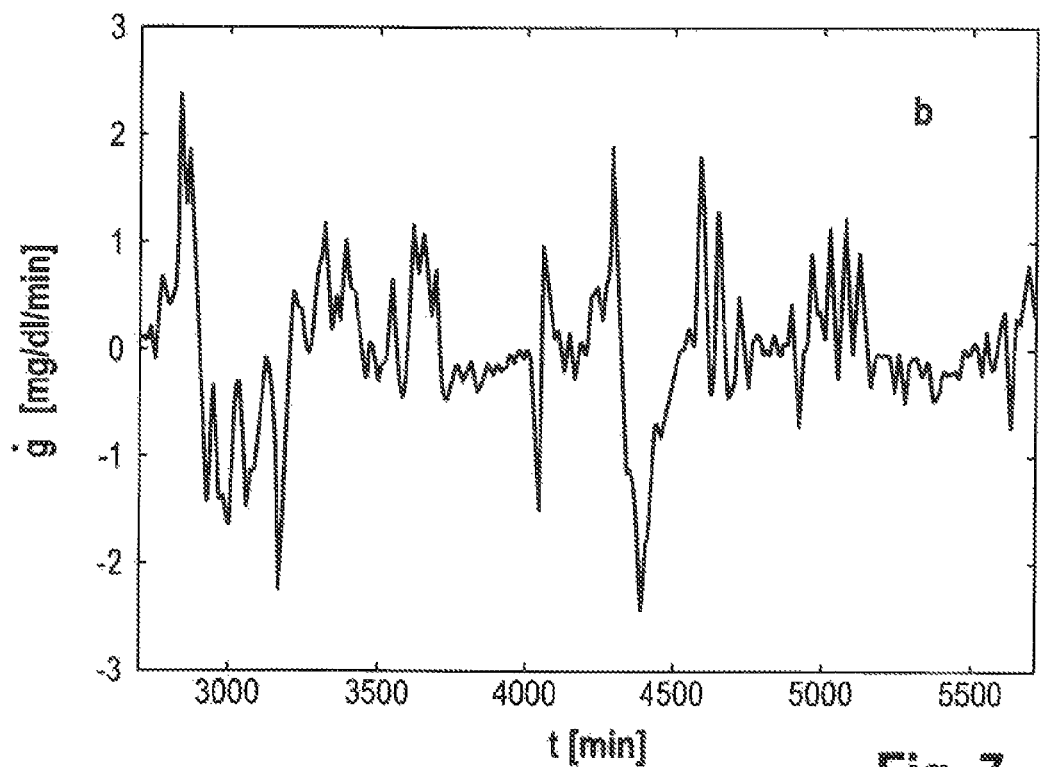
FIG. 7 shows the profile of the rate of change of the blood glucose concentration of the type 2 diabetic shown in FIG. 3.
Figure 8:
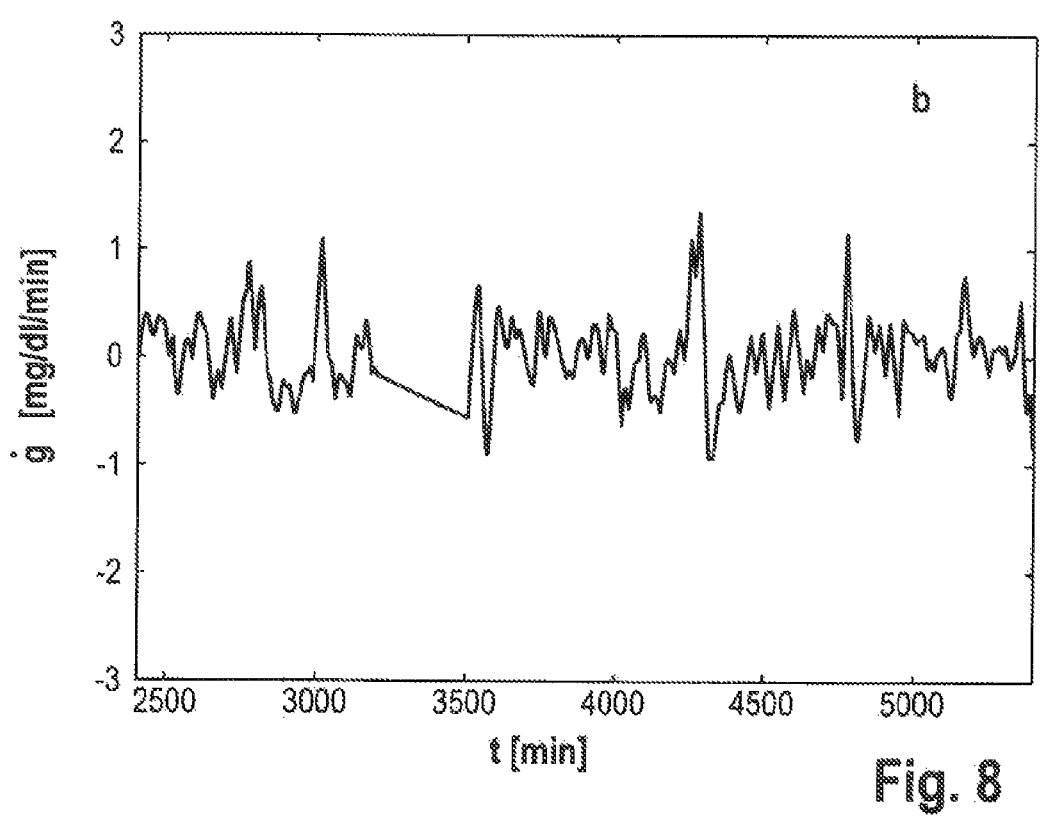
FIG. 8 shows the profile of the rate of change of the blood glucose concentration of the pre-type 2 diabetic shown in FIG. 4.

FIG. 10 shows a corresponding representation for a type 1 diabetic based on the data of FIGS. 2 and 6. As an essential difference to the representation shown in FIG. 9, it is evident that major parts of the trajectory show relatively little curvature only and the trajectory is distributed more or less evenly over the section of phase space shown here. In particular, no regulation point at which multiple loops of the trajectory intersect is evident.

The phase space representation of the data of a type 2 diabetic shown in FIG. 11 is similar to the phase space representation of the data of a type 1 diabetic as shown in FIG. 10 in that the loop structure of trajectories repeatedly passing through the regulation point, as is typical of a functioning regulatory mechanism, is lacking. Major parts of the trajectory shown in FIG. 11 show rather a wave-like structure without forming loops. In particular, no part of the phase space shown is characterized by a significantly higher density of data points. Moreover, FIG. 11 evidences in an exemplary fashion that it is also feasible to use parameters derived from state variables (e.g. concentration, rate of change) as coordinates.

Clear differences are evident when one compares the phase space representations of FIGS. 9 and 10, which are typical of a healthy subject and a type 1 diabetic, respectively, to the representation of the data points of the seemingly healthy pre-type 2 diabetic shown in FIG. 12.

The formation of loops is evident in the trajectory of a pre-type 2 diabetic shown in FIG. 12, which is similar in this respect to a healthy subject (FIG. 9). However, these loops do not intersect in a well-defined regulation point, which is situated approx. at (90 mg/dl; 0 mg/dl/min) in FIG. 9, but rather are distributed more or less evenly over an area between (80 mg/dl; 0 mg/dl/min) and (150 mg/dl; 0 mg/dl/min). Accordingly, the regulation point that is characteristic of a functioning regulatory mechanism is smeared out into an extended regulation area.

The maximal density of data points in a pre-determined volume element $\Delta V=\Delta x\Delta y$ of the phase space representation shown in FIG. 12 whereby $\Delta x=10$ mg/dl and $\Delta y=1$ mg/dl/min, for example, is significantly higher than in the phase space representations for diabetics (FIG. 10), but significantly lower than in a healthy subject (FIG. 9).

From these representations it is evident that the physician can discriminate, even with little training, between a pre-type 2 diabetic not yet showing the common symptoms of diabetic disease and a healthy subject on the basis of the phase space representation of data points of the glucose profile.

Figure 13:
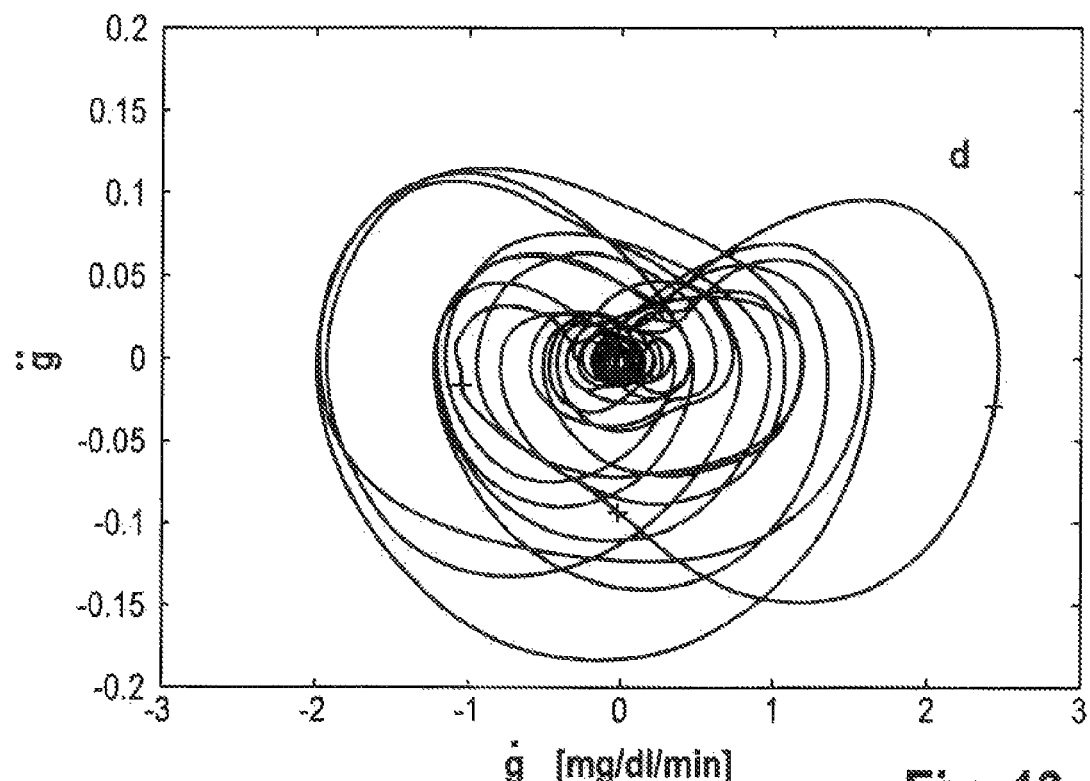
FIG. 13 shows another phase space representation based on the measuring values of the healthy subject shown in FIG. 1.
Figure 14:
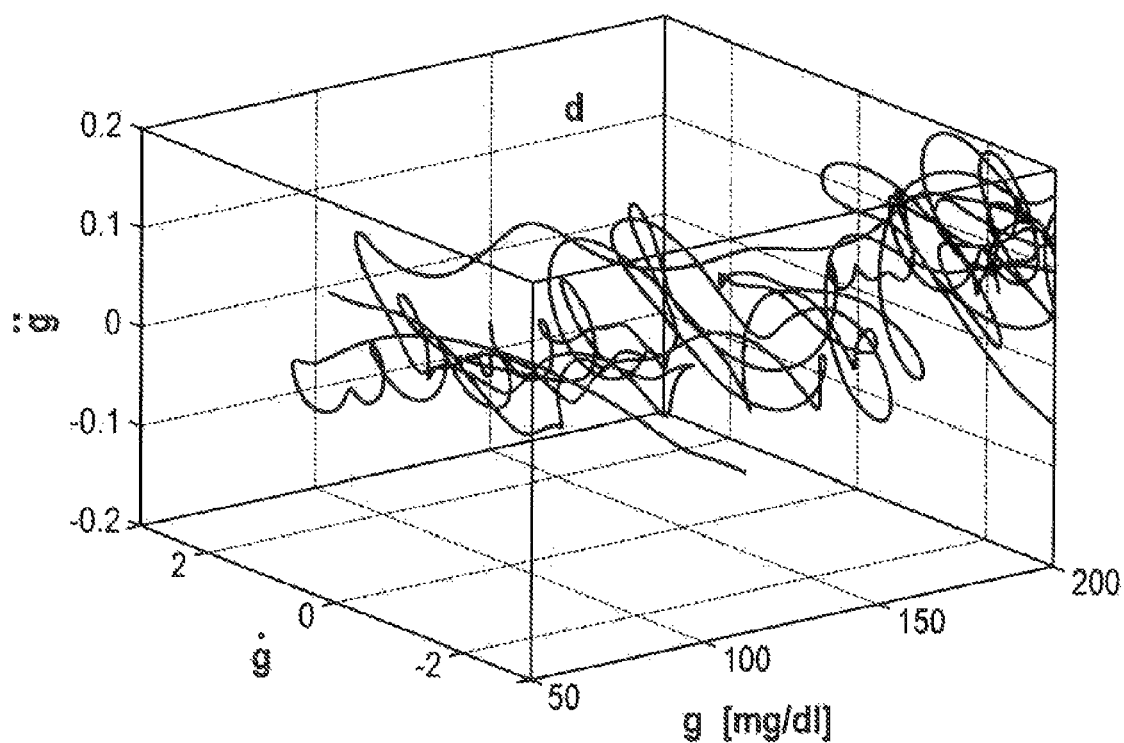
FIG. 14 shows another phase space representation based on the measuring values of the type 1 diabetic shown in FIG. 2.

The first and second derivative with respect to time of the blood glucose concentration (i.e. rate of change and acceleration) are used as phase space coordinates in FIGS. 13 to 16 as further example of a phase space representation that is well-suited for the present invention. In the case of FIG. 14, the blood glucose concentration itself was used as a phase space coordinate in addition to the two derivatives with respect to time for a three-dimensional phase space representation.

The phase space representation shown in FIG. 13 is based on the blood glucose concentration measuring values of a healthy subject shown in FIG. 1. Like in the phase space representation of the healthy subject shown in FIG. 9, loops that are characteristic of a functioning regulatory mechanism are evident in FIG. 13 also. These loops intersect in a regulation point at approx. (0 mg/dl/min; 0 mg/dl/min$^2$) such that the density of data points is significantly higher in a volume element $\Delta V=\Delta x$ times $\Delta y$ around the regulation point, whereby $\Delta x=0.2$ mg/dl/min and $\Delta y=0.03$ mg/dl/min$^2$.

Figure 15:
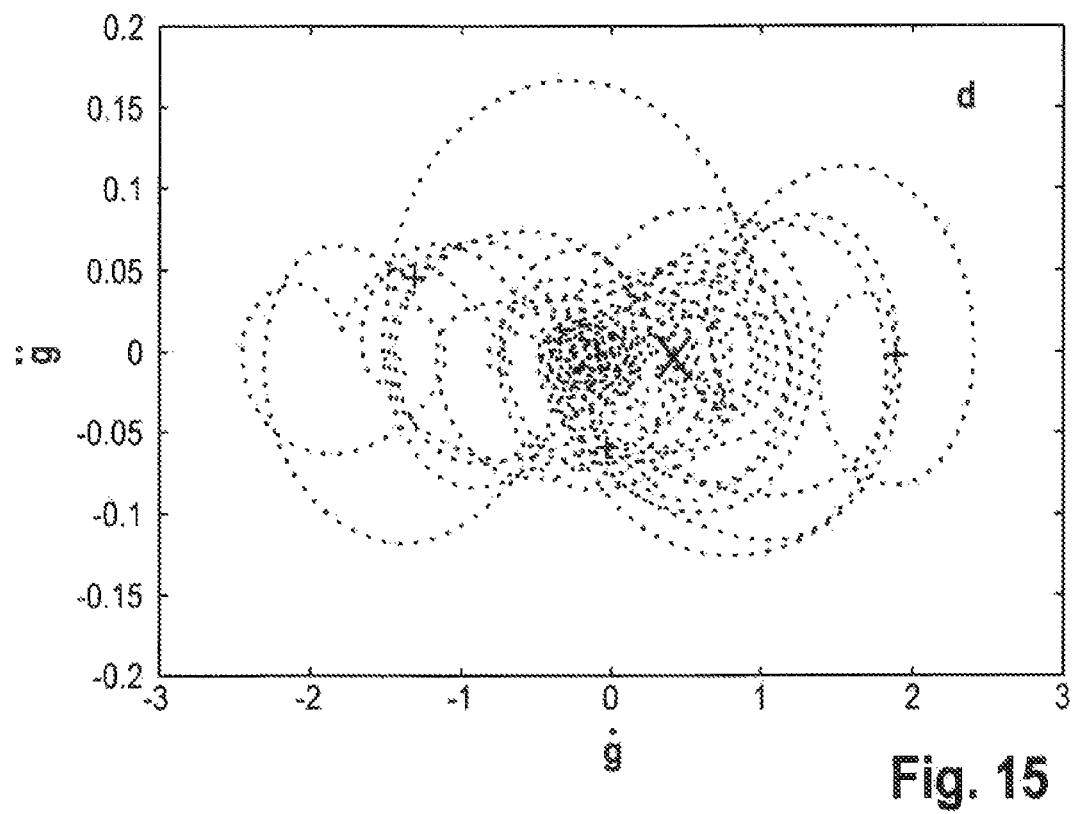
FIG. 15 shows another phase space representation based on the measuring values of the type 2 diabetic shown in FIG. 3.
Figure 16:
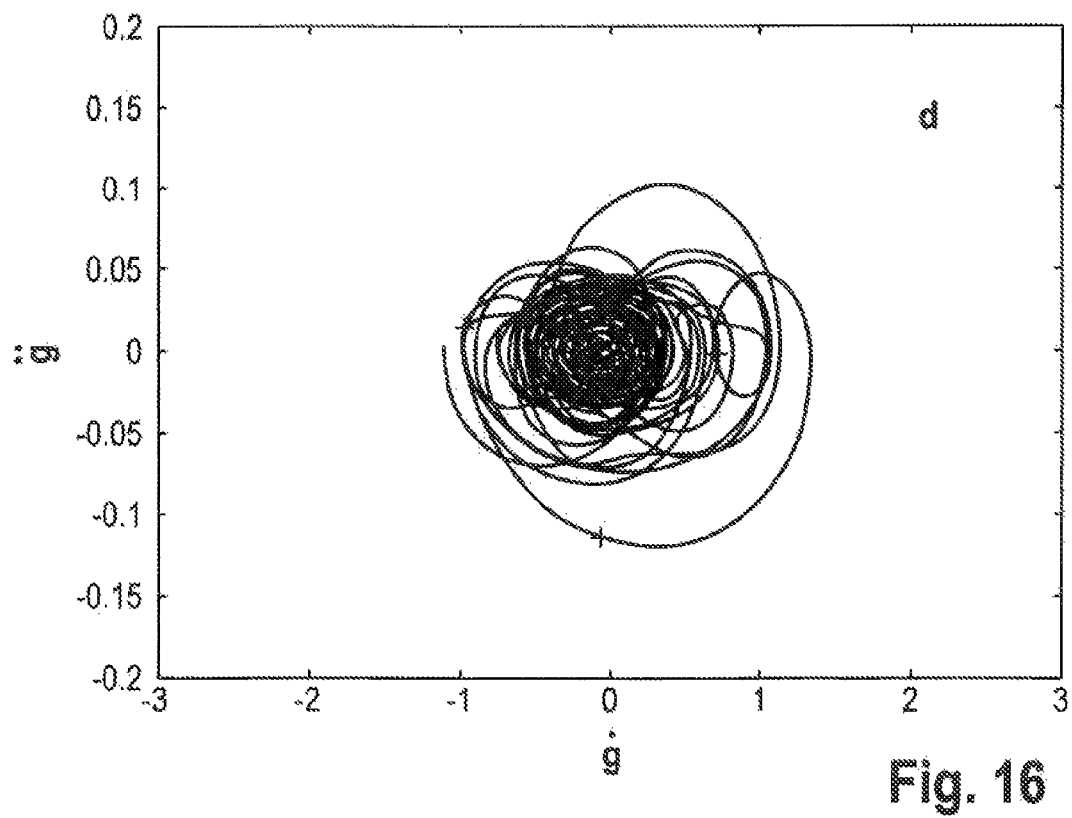
FIG. 16 shows another phase space representation based on the measuring values of the pre-type 2 diabetic shown in FIG. 4.

No formation of loops by the trajectory is evident in the phase space representations for diabetics (FIGS. 14 and 15). A regulation point is not evident at all or no more than barely in FIG. 14 and FIG. 15, respectively. In FIG. 15, a capital X marks, in addition, the center of gravity of the data points. Although some loop formation by the trajectory is evident in the corresponding phase space representation of the seemingly healthy pre-type 2 diabetic (FIG. 16), the volume area of increased data point density around the regulation point that is evident in FIG. 14 is expanded to an approx. 10-fold larger volume.

From the figures described here it is evident that data points can be processed by plotting in a phase space representation that can be provided to a physician as a diagnostic aid. Even by the unaided eye, it is feasible to recognize in a phase space representation characteristic particularities and draw conclusions with regard to the manifestation of a pathological disturbance of glucose metabolism.

As was illustrated above, suitable state variables for the description of the system of glucose metabolism are used as phase space coordinates. The coordinates for the application purposes of the present invention are the glucose concentration and its derivatives with respect to time, in particular in the form of delay coordinates. Of the derivatives with respect to time, the first derivative with respect to time (rate of change) is particularly well-suited. Obviously, functions whose variables are formed by one or more of the primary state variables are also well-suited.

From a comparison of FIGS. 9 to 12 and FIGS. 13 to 16 it is evident that particularities that are characteristic of health and/or disease states are largely independent of the choice of phase space coordinates. The trajectory forming loops and increased data point density existing around a regulation point are always indicative of a functioning regulatory mechanism and, therefore, healthy glucose metabolism. With progressing disease, the trajectories show a progressively lesser tendency to form loops and the maximal density of the data points around a regulation point decreases until, ultimately, a regulation point can no longer be discerned.

In the case of a phase space representation being used as a diagnostic aid, it is highlight by coloring an increased data point density that is characteristic of a regulation point and, therefore, of a functioning regulatory mechanism.

It is favorable in this context for the data points to be shown in a color that depends on the number of data points that are present in a pre-determined vicinity U of the respective data point.

According to a further feature of the present invention, the data points are processed by determining from them a disturbance parameter that is correlated to the severity of a disturbance of glucose metabolism. This disturbance parameter can be used in addition to or instead of plotting the data points in a phase space representation.

The disturbance parameter can be determined, for example, by statistical analysis of the data points. As illustrated above with regard to the phase space representations shown, a healthy subject has a relatively distinctly defined regulation point in the vicinity of which the density of data points is clearly increased. Upon the manifestation of a disturbance of glucose metabolism with pathological significance, this regulation point becomes increasingly less well-defined such that the maximal density of the data points decreases accordingly and, ultimately, the regulation point disappears altogether upon the manifestation of diabetic disease. Consequently, the maximal density of data points in phase space is an important criterion for statistical analysis. By means of statistical analysis, the disturbance parameter can be determined, for example, from the fraction of data points situated within a pre-determined vicinity U of a regulation point or from the maximal fraction of data points situated within a volume element of pre-determined size.

Another option of statistical analysis involves the determination of the main axes of an ellipsoid of variance and calculation of the disturbance parameter from the ratio of the main axes of the ellipsoid of variance.

An ellipsoid of variance can be calculated from the scattering of the data points in phase space with its main axes indicating the variance of the data points in the respective direction of phase space. The ratio of the main axes of a two-dimensional phase space representation, for example, as shown in FIGS. 9 to 13, can be used as a disturbance parameter. With, for example, LG and LV, being the lengths of the normalized (and therefore unit-less) main axes of the variance of blood glucose concentration or variance of the rate of change of the blood glucose concentration, LG/LV>1 in the case of the ellipsoid of variance of a pre-type 2 diabetic, whereas this ratio is less than or equal to 1 in the case of a healthy subject.

Performing a statistical analysis is advantageous in that a trajectory does not necessarily need to be recognizable, i.e. the blood glucose concentration does not necessarily need to be determined in sufficiently short intervals for a phase space representation to show which data points are consecutive (in terms of measuring time). In summary, it can be concluded that a statistical analysis makes use of the fact that the data points are significantly more densely spaced around a regulation point in a healthy subject as compared to a person afflicted by diabetes. With progressing disease, the regulatory mechanism for adjustment of the blood glucose concentration deteriorates to the effect that more and more data points can be found to be situated far from the regulation point.

Another option for the calculation of a disturbance parameter is the analysis of a cross-prediction of a trajectory profile. In this procedure, model parameters are optimized to generate a prediction function that can be used to approximate the profile of a trajectory to be analyzed in an area of the phase space. In the simplest case, the prediction function is a simple extrapolation of a pre-determined section of the trajectory.

In a cross-prediction, the prediction function obtained by adapting the optimization parameters for a trajectory to be analyzed is used to predict a reference trajectory in the corresponding area of phase space. This is used, for example, to adapt a prediction function to the trajectory of the data of a patient to be investigated and the function thus obtained is used to predict a trajectory of a healthy subject and of a diabetic patient. The magnitude of the error between the trajectory calculated with the prediction function obtained by this procedure and the trajectory of the healthy subject or of the diabetic indicates how far the health status of the patient to be investigated has progressed away from the healthy ideal state and approximated the state of a diabetic.

Figure 17:
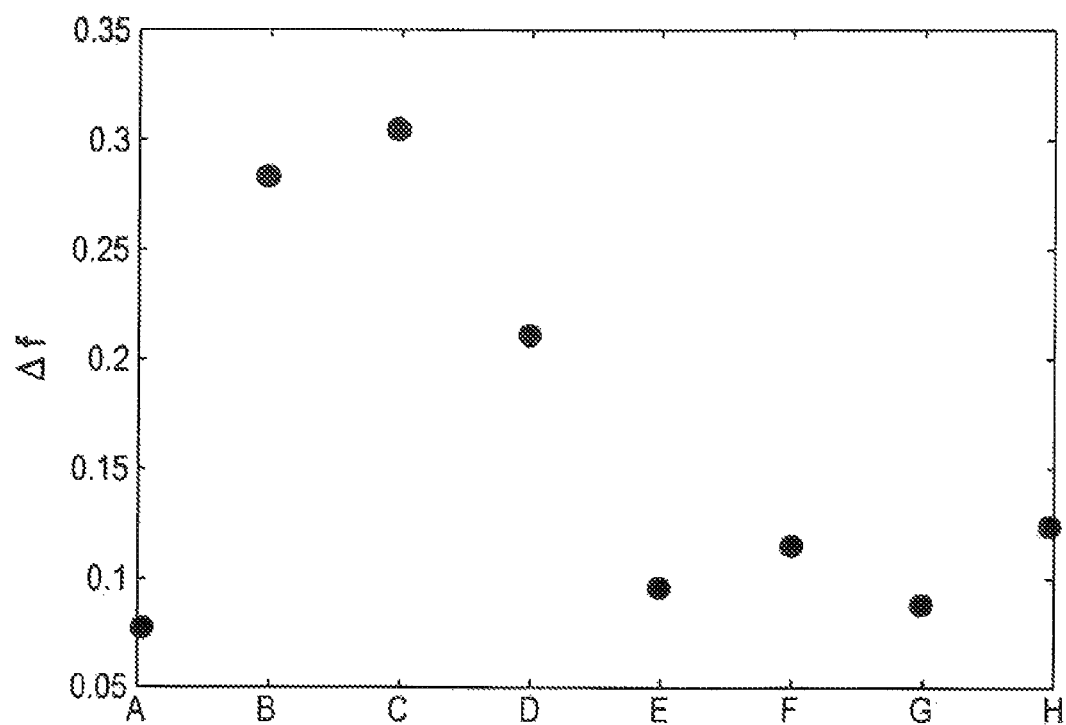
FIG. 17 shows results of a cross-prediction for various data sets.

As an example of this procedure, FIG. 17 shows the prediction error Δf for a test data set A that was obtained from a cross-prediction. In the process, data sets A to H were used as reference data sets. As expected, a very small prediction error is obtained when the test data set A is also used as reference data set in the cross-prediction. Applying the reference data sets B to H to the test data set, somewhat larger prediction errors Δf are obtained with reference data sets E to H and significantly larger prediction errors Δf are obtained with reference data sets B to D. In the example shown, data sets B to D were determined on healthy subjects and data sets E to H were obtained on type 2 diabetics. Accordingly, the prediction error Δf shown in FIG. 17 can be used to draw a conclusion for test data set A with regard to the presence of type 2 diabetes.

Another option for determining a disturbance parameter involves a geometric or differential-geometric analysis of the trajectories formed in phase space by the data points. An analysis of this type utilizes the fact that the blood glucose concentration returns to its regulation point after meals or physical exercise the faster, the better the regulation of the blood glucose concentration functions. Accordingly, in a healthy subject, the trajectories are much more strongly curved than in a diabetic. In particular, the trajectories form approximately circular loops in a healthy subject, whereas they take the shape of progressively eccentric ellipsoids with advancing disturbance of the regulation of glucose metabolism. For geometric analysis, the individual loops can therefore be viewed as approximative ellipsoids and the eccentricity of these ellipsoids as a measure of the severity of disease.

Figure 18:
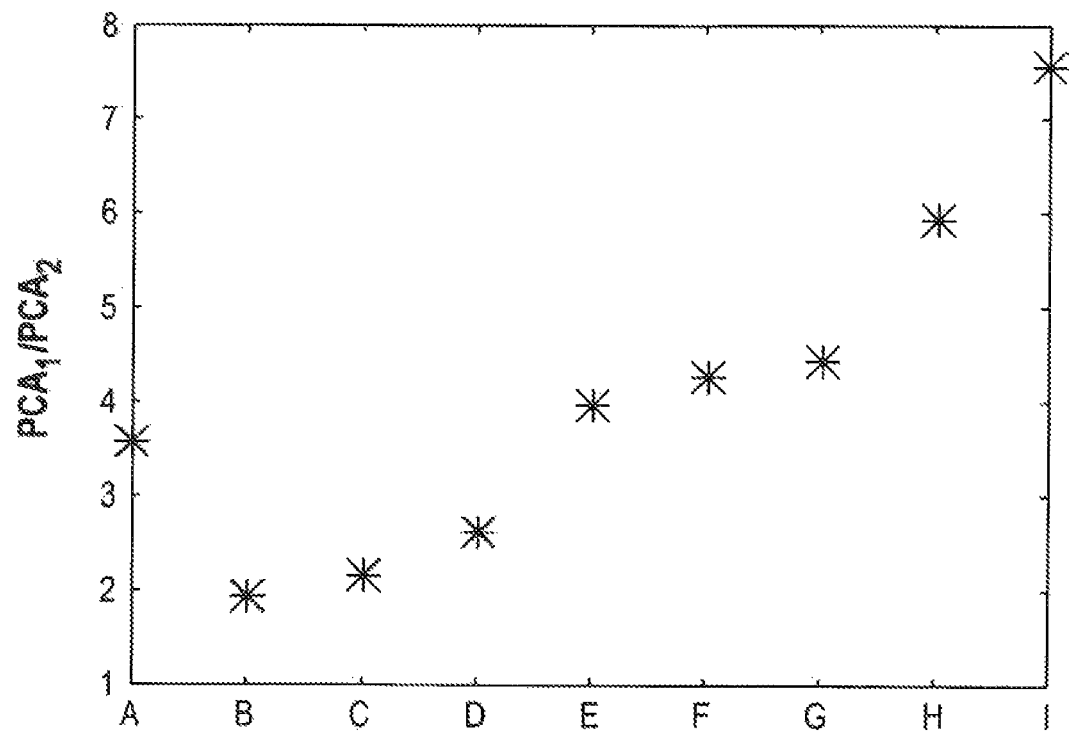
FIG. 18 shows values of a disturbance parameter for various data sets.

One example of a disturbance parameter obtained by geometric analysis is shown in FIG. 18 for data sets A to 1. In this context, the ratio of the lengths of the first and second main axis determined by main component analysis of phase space was used as disturbance parameter. Data set A was determined on a pre-diabetic, data sets B to D on healthy subjects, data sets E to I on type 2 diabetics differing in the status of their glucose metabolism. While endogenous insulin secretion is still sufficient in the patients producing data sets E to G, this is no longer true in the case of the patients producing data sets H and I.

FIG. 18 shows that data points in phase space coordinates can be used to determine a disturbance parameter that allows not only clear differences between healthy subjects and diabetics to be observed, but also is suitable for identifying various stages of a diabetic disease. For this reason, the disturbance parameter can also be used as staging parameter in a process of staging. In the example shown, the disturbance parameter takes a value of approx. 4 to 5 in the case of type 2 diabetics in an early stage of the disease. In this early stage of disease, insulin secretion is still sufficient. With progressing diabetic disease, insulin secretion ceases and the disturbance parameter takes a value of 6 or more. A disturbance parameter taking a value higher than 7 that is obtained from the ratio of the first and second main component (PCA1/PCA2) is associated with cession of counter-regulation in the presence of hypoglycemia.

Figure 19:
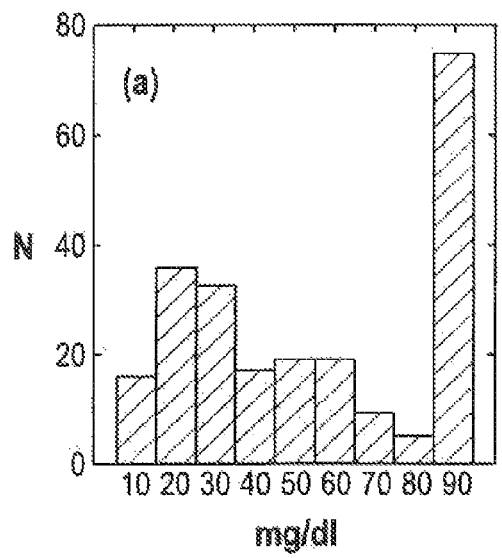
FIG. 19 shows a histogram of the distribution of radii of curvature of trajectories in a partial area of the phase space for the example of a type 2 diabetic.
Figure 20:
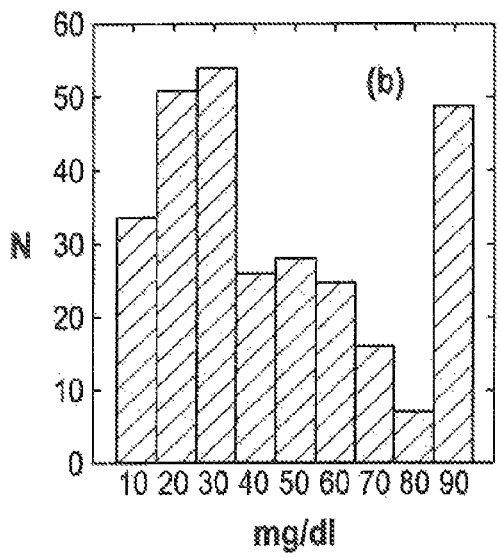
FIG. 20 shows a histogram of the distribution of radii of curvature of trajectories outside the partial area of FIG. 19.

Another example of a differential-geometric analysis of a phase space representation is shown in FIGS. 19 and 20. These figures show histograms of the distribution of radii of curvature of the trajectories of a type 2 diabetic which were obtained in delay coordinates with a delay time of fifteen minutes. Each of the plot shows the number of loops with the indicated radius of curvature versus the radius of curvature in units of mg/dl. The histogram shown in FIG. 20 relates to the partial area of phase space that is occupied by the trajectories at a time of rapid changes in blood glucose concentration after a meal. FIG. 19 shows for the same patient in the same fashion a histogram of the frequency distribution of radii of curvature of trajectories in a second part of phase space that is occupied by the trajectories at a time of slow changes of the blood glucose concentration, e.g. several hours after a meal.

In a phase space representation in delay coordinates, data points that are associated with a rapid change in the blood glucose concentration are situated at a greater distance to the main diagonal. In the example shown in FIGS. 19 and 20, trajectories whose data points are situated more than 5 mg/dl from the main diagonal were assigned to a first rapid phase of insulin secretion, to which FIG. 19 refers. Accordingly, FIG. 20 shows results for trajectories whose data points are situated less than 5 mg/dl from the main diagonal. By this means, various mechanisms of the body's intrinsic regulatory mechanism can be investigated. In a first phase of insulin secretion, insulin is released very rapidly in response to the intake of food. After the first phase of insulin secretion follows a second slower phase of insulin secretion. It is therefore evident from FIG. 20 how well the body's intrinsic regulatory system responds to a rapid increase of blood glucose values and how well the first phase of insulin secretion works. FIG. 19 shows in corresponding fashion how well the slower regulatory mechanism works as the second phase of insulin secretion.

The smaller the radius of curvature of the trajectories, the more rapidly the blood glucose concentration is restored to its nominal value by the body's intrinsic regulatory mechanism. With the progression of a diabetic disease, larger radii of curvature are evident at increasing frequency in a histogram such as is shown in FIGS. 19 and 20 such that a disturbance parameter for a staging can be derived also from a histogram.

It is evident from FIG. 19 that the second phase of insulin secretion, i.e. the slow regulatory mechanism, in the type 2 diabetic investigated is already strongly disturbed as evidenced by the increased frequency of trajectories with a large radius of curvature. The first phase of insulin secretion, i.e. the rapid regulatory mechanism, shows to be disturbed to a significantly lesser degree as is evident from the fact that trajectories with a small radius of curvature occur more frequently overall in FIG. 20 as compared to trajectories with a very large radius of curvature. It can thus be concluded that the body's intrinsic regulatory mechanism is partially retained (yet) in the type 2 diabetic investigated, which allows for adapted therapy according to staging.

Figure 21:
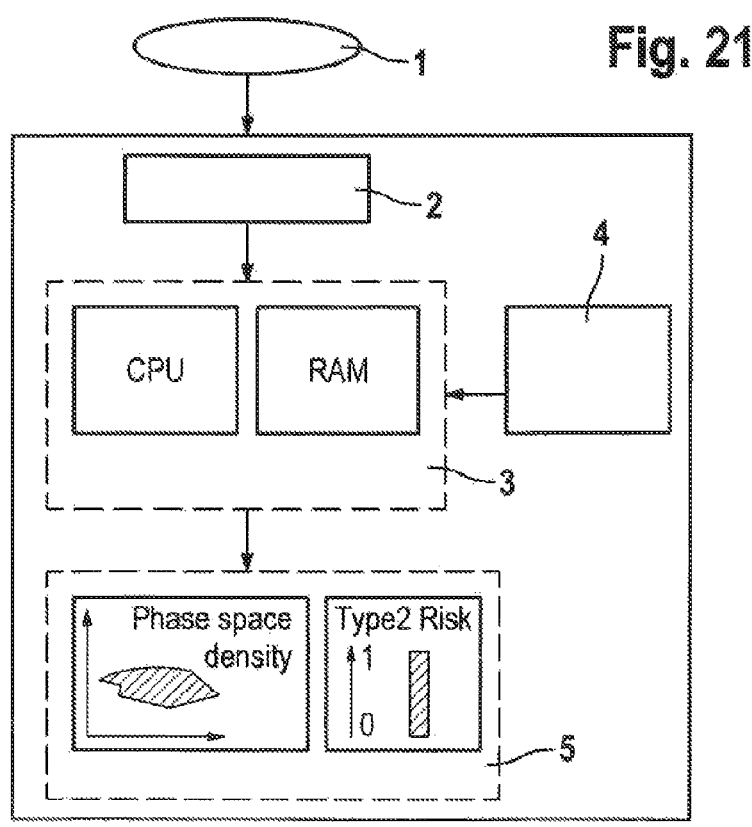
FIG. 21 shows a block diagram of a system according to the invention for investigation of glucose metabolism.

FIG. 21 shows a block diagram of the system for investigating glucose metabolism according to the invention. The system comprises a measuring unit 1 that is used to measure the blood glucose concentration g(t1) to g(tn) at time points t1 to tn that are distributed over a period of at least four hours, preferably at least six hours. Preferably, the measuring unit 1 is an implanted sensor allowing the blood glucose concentration to be measured, for example by spectroscopic means. The measuring values are transmitted, preferably by wireless means, via a reception unit 2 to an analytical unit 3. The core of the analytical unit consists of a microprocessor (CPU) and an electronic storage device (RAM).

The analytical unit 3 is used to determine data points in phase space coordinates from the measured blood glucose concentrations g(t1) to g(tn). These are then processed in the fashion described above, on the one hand by displaying them in a phase space representation by means of a display unit 5, and on the other hand by determining from the data points a disturbance parameter that is correlated to the severity of a disturbance of glucose metabolism. This disturbance parameter is also displayed by the display unit 5. In the exemplary embodiment shown, the disturbance parameter takes a value between 0 and 1. The disturbance parameter indicates the stage of glucose metabolic disease that is likely to be manifest. Consequently, the disturbance parameter can be used not only to decide whether or not a diabetic disease is manifest, but also to decide which stage of disease is manifest in the patient. By this means, the system facilitates optimal therapy adapted to the individual needs of the corresponding patient. A system according to the invention preferably comprises a database that is used to determine for a pre-determined disturbance parameter a therapy recommendation which is then displayed to the physician. In addition, the system comprises an input unit 4 that can be used, for example, to enter control commands as part of a maintenance process.

Preferably, the system also includes an implant (not shown) with a storage reservoir for insulin and a device, e.g. a micropump, for the controlled release of insulin into the bloodstream of a patient, i.e. an artificial pancreas. The system according to the invention can be used to monitor and optimize the operation of this implant in that it triggers an alarm signal as soon as the disturbance parameter thus determined deviates by more than a pre-determined tolerance from a pre-determined nominal value, which is equal to a disturbance parameter of 0 in the exemplary embodiment shown.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for investigating a glucose metabolism of a human being for particularities, the method comprising:
    measuring, using a sensor, a glucose concentration g(t1) to g(tn) of a body fluid at time points t1 to tn that are distributed over a period of at least six hours and are consecutive with time intervals of less than 10 minutes;
    determining, using a microprocessor, data points in phase space coordinates from the glucose concentration g(t1) to g(tn); and
    processing, using the microprocessor, the data points to identify particularities of the glucose metabolism of the investigated human being;
    wherein the processing step includes performing a statistical analysis of the data points situated within a phase space boundary of a predetermined size having at least two dimensions to determine a disturbance parameter that indicates a severity of a disturbance of glucose metabolism and indicates a stage of a disease of glucose metabolism.

2. The method according to claim 1, wherein the body fluid is blood.

3. The method according to claim 1, wherein the time points t1 to tn are consecutive with time intervals of less than 5 minutes.

4. The method according to claim 1, wherein the determining step includes the step of determining data points in a two dimensional phase space coordinate system from the glucose concentration.

5. The method according to claim 1, wherein the data points are processed by plotting in a graphic phase space representation.

6. The method according to claim 5, wherein an increased density of data points in the graphic phase space representation is highlighted by coloring.

7. The method according to claim 6, wherein the data points are shown in a color that depends on the number of data points that are present in a pre-determined vicinity U of a first data point.

8. The method according to claim 6, wherein different symbols are used in areas of increased data point density as compared to regions of lower density.

9. The method according to claim 5, wherein a trajectory described by the data points is displayed.

10. The method according to claim 1, wherein delay coordinates are used as phase space coordinates.

11. The method according to claim 10, wherein a delay time of between 10 minutes and 90 minutes, preferably between 15 minutes and 30 minutes, is selected for the delay coordinates.

12. The method according to claim 1, wherein the disturbance parameter is determined from the fraction of data points situated within a pre-determined vicinity U of a regulation point.

13. The method according to claim 1, wherein the disturbance parameter is determined from the ratio of the main axes of an ellipsoid of variance of the data points.

14. The method according to claim 1, wherein a trajectory in phase space described by a sequence of data points is analyzed in order to determine the disturbance parameter.

15. The method according to claim 14, wherein the disturbance parameter is determined from a curvature of a loop of the trajectory.

16. The method according to claim 15, wherein the loop of the trajectory is approximated by an ellipse and the disturbance parameter is determined from a ratio of main axes of the ellipse.

17. The method according to claim 1, wherein the disturbance parameter is determined by means of a cross-prediction.

18. The method according to claim 1, wherein the disturbance parameter is correlated to a probability of a diabetic disease.

19. A system for investigating a glucose metabolism of a human being for particularities, the system comprising:
- means for measuring a blood glucose concentration $g(t1)$ to $g(tn)$ at time points $t1$ to $tn$ that are distributed over a period of at least four hours; and
- means for determining data points in phase space coordinates from the glucose concentration $g(t1)$ to $g(tn)$;
- wherein the determining means is used to process the data points to identify a boundary having at least two dimensions in phase space having the data points therein which corresponds to a particularity of the glucose metabolism of the investigated human being and indicates a stage of a disease of glucose metabolism.

20. The system of claim 19, wherein the time points $t1$ to $tn$ are distributed over a period of at least six hours.

21. The system according to claim 19, wherein the system further comprises a display facility for displaying the data points thus determined in a phase space representation.

22. The system according to claim 19, wherein the determining means is used to determine from the data points a disturbance parameter that is correlated to a severity of a disturbance of glucose metabolism.

23. The system according to claim 22, wherein the disturbance parameter is used in conjunction with therapy data stored in a database to prepare and output a therapy recommendation.

24. The system according to claim 19, wherein the system comprises an implant with a storage reservoir for insulin and a micropump for the controlled release of insulin into the bloodstream of a patient, whereby the determining means triggers an alarm signal as soon as the disturbance parameter deviates by more than a pre-determined tolerance from a pre-determined nominal value.

25. A method for investigating a glucose metabolism of a human being for particularities, the method comprising:
- measuring, using a sensor, a glucose concentration $g(t1)$ to $g(tn)$ of a body fluid at time points $t1$ to $tn$ that are distributed over a period of at least six hours and are consecutive with time intervals of less than 10 minutes;
- determining, using a microprocessor, data points in phase space coordinates from the glucose concentration $g(t1)$ to $g(tn)$; and
- processing, using the microprocessor, the data points to identify particularities of the glucose metabolism of the investigated human being;
- wherein the processing step includes performing a statistical analysis of the data points to determine a disturbance parameter that indicates a severity of a disturbance of glucose metabolism, the disturbance parameter being determined from a curvature of a loop of a trajectory in phase space described by a sequence of data points, the loop being approximated by an ellipse having main axes, and
- wherein the disturbance parameter is determined from the curvature of the loop by determining a ratio of the axes.

26. The method of claim 1, wherein the phase space is a volume having three dimensions.

27. The method of claim 7, wherein the first point is a regulation point.

28. The method according to claim 1, wherein a function of the blood glucose concentration and/or at least one of its derivatives with respect to time are used as phase space coordinates.

29. The method according to claim 28, wherein the glucose concentration is one of the phase space coordinates.

30. The method according to claim 28, wherein a rate of change of the glucose concentration is one of the phase space coordinates.

* * * * *